United States Patent [19]

Arnold

[11] Patent Number: 5,252,122
[45] Date of Patent: Oct. 12, 1993

[54] IONIC BOND BETWEEN AMALGAM AND GLASS IONOMER

[75] Inventor: Thomas J. Arnold, Winslow, Ind.

[73] Assignee: Mion International Corporation, Winslow, Ind.

[21] Appl. No.: 942,375

[22] Filed: Sep. 9, 1992

Related U.S. Application Data

[63] Continuation of Ser. No. 748,679, Aug. 22, 1991, abandoned.

[51] Int. Cl.⁵ ........................... C09K 3/00; A61C 5/00
[52] U.S. Cl. ................................... 106/35; 433/228.1
[58] Field of Search .................. 106/35; 433/228.1

[56] References Cited

U.S. PATENT DOCUMENTS

| | | | |
|---|---|---|---|
| 3,676,112 | 7/1972 | Muhler | 15/173 R |
| 3,933,961 | 1/1976 | Burns | 264/111 |
| 4,064,629 | 12/1977 | Stoner et al. | 433/217.1 |
| 4,654,007 | 3/1987 | Sigler et al. | 433/236 |
| 4,684,347 | 8/1987 | Palaghias | 433/228.1 |
| 4,738,722 | 4/1988 | Ibsen et al. | 106/35 |
| 4,813,871 | 3/1989 | Friedman | 433/90 |
| 4,872,936 | 10/1989 | Engelbrecht | 156/307.3 |

OTHER PUBLICATIONS

Illustrated Dictionary of Dentistry, W. B. Saunders Company, pp. 37-38, Jun. 1982.
Aboush et al., The bonding of glass-ionomer cements to dental amalgam, British Dental Journal, 1989; 166:255-257.
Mojan et al., Maximum Bond Strength of Dental Luting Cement to Amalgam Alloy, Journal of Dental Research, Nov. 1989; 68(11):1545-1549.
Aboush et al., An evaluation of the bonding of glass-ionomer restorations to dentine and amalgam, British Dental Journal, 1986;161:179-184.
Gilmore et al., Operative DENTISTRY, C. V. Mosby Company, 1973; pp. 196-200, 279-281.
Geristore: A Pediatric/Geriatric Restorative, video tape by Dr. Ronald Jordan, American Society for Clinical Research, No. 1006780, V1.0. (no date).
Hotz et al., The Bonding of Glass Ionomer Cements to Metal and Tooth Substrates, British Dental Journal, 1977; 142; 41-47.
Scherer et al., Reinforced Glass Ionomer Cement vs. Zinc Phosphate Cement, 18th Annual Session of Assoc. for Dental Research, San Francisco, Jan. 1990.
Johnson et al., Dentin Bonding Systems: A Review of Current Products and Techniques, The Journal of the American Dental Assoc., 1991; 122:34-41.
Matis, et al., How Finishing Affects Glass Ionomers, Journal of the American Dental Assoc., 1991: 122:43-46.
New Era of Composite Bonding, Dentistry Today, Jun./Jul. 1991, pp. 32,34.
New Products—Adhesive System, Dental Products Report, Sep. 1991.
Shofu Advertisement, Dental Products Report, Sep. 1991, p. 65.
Dentistry Techniques, Dental Products Report, Sep. 1991, pp. 74-75.
Retentive Pins . . . Are they everything they're cracked up to be?, Advertisement, American Dental Assoc. News, 1991; 22, 14: p. 15.
Amalgambond—The first bonding agent for amalgam, Advertisement, American Dental Assoc. News, 1991; 22,13: p. 28.

(List continued on next page.)

*Primary Examiner*—Mark L. Bell
*Assistant Examiner*—Margaret Einsmann
*Attorney, Agent, or Firm*—Baker & Daniels

[57] ABSTRACT

Wet glass ionomer cement is applied to a tooth lesion. Before the cement hardens, wet amalgam is applied on top of the glass ionomer cement. The glass ionomer bonds to the tooth, and the interface of the wet cement and wet amalgam allows strong ionic bonds to form between the glass ionomer cement and the amalgam, to provide an exceptionally strong bond between the amalgam and the tooth.

17 Claims, No Drawings

OTHER PUBLICATIONS

Starting today, you may never have to re-cement again ... ever. Advertisement, Dentistry Today, 1991; 10,6: p. 17.

Staninec et al., *Bonding of Amalgram to tooth structure:* Tensile adhesion and microleakage tests; Journal of Prosthetic Dentistry; 59:4; Apr. 1988; pp. 397-402.

Rueggeberg et al., *Bond Strength of Panavia EX to Dental Amalgam;* International Journal of Prosthodontics; 2:4; pp. 371-375, 1989.

Torii et al., *Inhibition in Vitro of Caries around amalgam Restorations by Bonding Amalgam to Tooth Structure;* Operative Dentistry; 14; 1989; pp. 142-148.

Shimizu et al., *Bond Strength between Amalgam and Tooth Hard Tissues with Application of Flouride, Glass Ionomer Cement and ...*, Dental Materials Journal; 52; 1986; pp. 225-232.

Varga et al., *Bonding of Amalgam Filling to Tooth Cavity with Adhesive Resin;* Dental Materials Journal; 5:2; 1986; pp. 158-164.

Lacy et al., *The bonded amalgam restoration;* Quintessence International; 20:7; 1989, pp. 521-524.

Cooley et al., *Bond strength of resin to amalgam as affected by surface finish;* Quintessence International; 20:4; pp. 237-239, 1989.

Hibler et al.; *Bond Strength Comparisons of Repaired dental Amalgams;* Quintessence International; 19:6; 1989; pp. 411-415.

Yu et al., *Experimental use of a bonding agent to reduce marginal microleakage in amalgam restorations;* Quintessence International; 18:11; 1987; pp. 783, 787.

Colon et al., *Les amalgames colles: technique diretc et indirecte;* Revue D'Odonto Stomatologie; 16:1; 1987; pp. 9-18.

Warren et al., *Bonding amalgam to glass ionomer with PAA;* Dental Materials; 4; 1988; pp. 191-196.

Stevenson, *Modified Bonded Amalgam Technique* (letter to the editor); British Dental Journal; Dec. 24, 1983; p. 401.

*The Government Chemist Plays Host;* British Dental Journal; Apr. 23, 1983; p. 268.

Braden, *The Effect of Technology on Clinical Practice,* Jul 1 to 3, 1983.

*Effects of Polycarboxylate and Glass-Ionomer cements on Stainless Steel crown Retention;* British Dental Journal; p. 218, 1983.

Pearson, *Finishing of Glass-Ionomer Cements;* British Dental Journal; 155; 1983; pp. 226-228.

*Opacity of Glass-Ionomer Cements,* 1983, Acta Odontol Scand 41:155-157.

Prodger et al., *ASPA Adhesion Study;* British Dental Journal; 143, 1977; pp. 266-274.

*Dentist's Desk Reference: Materials, Instruments and Equipment;* American Dental Association; 1981, pp. Preface and 84-54.

Expansion of the Acceptance Program for dental materials and devices; glass ionomer cements; JADA; 99; Aug. 1979; pp. 227-228.

Reported Sensitivity to glass ionomer luting cements; JADA; 109; Sep. 1984; p. 476.

Status report on the glass ionomer cements; JADA; 99; Aug. 1979; pp. 221-224.

Dentist's Desk Reference; *Materials, Instruments and equipment;* American Dental Association; 1983; pp. Preface and 118-119.

Gilmore et al., Operative Dentistry; 1973; pp. 64-95.

Cardosa et al., *Low-Silver amalgam restorations; A two-year clinical evaluation,* Dental Materials, Jul. 1989; 5:277-80.

Osborn, *Clinical Assessment of 14 amalgam alloys,* General Dentistry, May-Jun. 1990:206-208.

Powell et al., *Effect of Admixed Indium on Mercury Vapor Release from Dental Amalgam,* Journal of Dental Research, Aug. 1989; 68(8):123;123.

Mercurial Debata, Science; d55(13):1356-1357, 1992.

Fasbinder et al., *Tensile Bond Strength of Dental Adhesives to Dentin and Enamel,* Dental Materials, Jul. 1989; 5:272-276.

Curtis, *The Use of Dental Amalgam—An Art or a Science?,* 1992 Jul./Aug. Dental Update pp. 239-245.

Watson, *The interfacial region of the tooth/glass ionomer restoration: A confocal optical microscope study,* Am J Dent 1991; 4: 303-310.

IONIC BOND BETWEEN AMALGAM AND GLASS IONOMER

This is a continuation of application Ser. No. 07/748,679, filed Aug. 22, 1991, now abandoned.

FIELD OF THE INVENTION

This invention relates to a system for the restoration of lesions in living teeth, and in particular, to a system for chemically bonding amalgam to dentin.

BACKGROUND OF THE INVENTION

Because conventional fillings rely purely on mechanical retention to the tooth, they are not suitable in instances when a tooth is severely decayed and has little structure left to which the filling may be attached. A conventional filling in a tooth with even only a moderate amount of decay may fail over time due to recurrent decay, lack of retention, or continued stress breakdown of the remaining tooth structure. Therefore, the patient is often faced with the choice of removing the tooth or the application of a crown.

In some instances, retentive pins are used to affix restorations to a tooth. However, pins tend to weaken the restoration, create stresses within the tooth, and may also result in pulpal exposure. Thus, it is desirable to provide a dental restoration system which does not utilize pins or other similar mechanical mechanism so as to limit the stress placed on the tooth.

Many types of materials have been used to affix a restoration to a tooth, including glass ionomer cement and dentin bonding systems. Glass ionomer cement bonds to tooth structure dentin and has been used for restorative materials, cavity liners, bases, and crown cements. As a crown cement, the glass ionomer cement is mixed, placed into the crown and, before the cement hardens, the crown is placed over the prepared tooth. As the glass ionomer cement hardens, the crown is retained on the tooth, and, after complete hardening of the cement, an excellent bond between the tooth and crown is formed. In other situations, glass ionomer cement may be applied to a tooth and allowed to harden to form a liner or base on which the amalgam may then be applied to restore the tooth using conventional techniques.

Studies have been conducted to determine the capability of glass ionomer cements to adhere to various materials, including the tests disclosed in Hotz, et al., *The Bonding of Glass Ionomer Cements to Metal and Tooth Substrates*, British Dental Journal, 1977; 142: 41-47. This study demonstrated that glass ionomer cement bonds well with dentin and enamel, and also adheres to some cast solid metals. Adherence to a cast solid metal is most successful when the surface of the metal is first etched with an acid, such as citric acid, before applying the glass ionomer cement.

Results of studies such as Hotz et al., have provided a basis for the use of glass ionomer cements in various dental procedures. For example, in U.S. Pat. No. 4,654,007, a layer of glass ionomer cement is applied to a tooth before attaching a porcelain restoration. After proper hardening of the cement, the cement is etched with an acid to create microscopic surface irregularities or tubules, which facilitate mechanical retention of the porcelain restoration to the tooth. The method disclosed in U.S. Pat. No. 4,738,722 is similar in that the glass ionomer cement disclosed is hardened and etched with an acid before the restoration material is placed into the cavity preparation. This method protects the pulp of the tooth by providing a layer of glass ionomer cement above the pulp.

The current restoration methods using glass ionomer cements have proven to be successful in restoring significant lesions. For example, Matis, et al., *How Finishing Affects Glass Ionomers*, 1991; 122: 43-46, preformed a five year study to determine the effectiveness of restorations involving the use of glass ionomer cements finding that the glass ionomer cements are outstanding in their retentive capability. Also, researchers continue to improve the retention capability of the cements. For example, the polymerizable cement mixtures disclosed in U.S. Pat. No. 4,872,936 demonstrate increased mechanical strength, lower solubility, and have no outstanding separation phenomena.

However, one shortcoming of using glass ionomer cements in present restorative techniques is the glass ionomer cement must be allowed to harden before it is etched with acid. This results in an undesirable time delay, and the risk that tooth damage to the nerve might occur while etching the hardened glass ionomer. Therefore, it is desirable to develop a dental restoration system which is efficient and requires relatively little time to perform.

In instances when hardened glass ionomer is used as a base for amalgam, studies show that the glass ionomer shrinks, leaving a slight 60-80 um gap between the hardened glass ionomer and the hardened amalgam. Scherer, *Reinforced Glass Ionomer Cement vs. Zinc Phosphate Cement*, 18th Annual Session of the American Association for Dental Research, San Francisco, Calif. Thus, the hardened glass ionomer does not bond the amalgam to the tooth.

Dentin bonding systems which utilize cements other than glass ionomers, such as those discussed in Johnson, et al., *Dentin Bonding Systems: A Review of Current Products and Techniques*, The Journal of the American Dental Association, 1991; 122: 34-41, have recently become available. The cements used in these dentin bonding systems are applied to the tooth prior to filling the tooth or to the application of a restoration. However, before being applied to the tooth, the tooth is etched with an acid to create tubules to which the dentin bonding systems are micromechanically bonded. These systems have not been well-received due to the risk of pain and damage if the acid contact sensitive dental nerves. In fact, Johnson et al. identifies several cautions in the use of dentin bond systems, and in fact, suggests the use of a protective liner for deep lesions. Therefore, it is desirable to develop a dental restoration system which does not require etching of the tooth or of the cement.

It is also known to fill a tooth lesion with composite materials, which may include a glass ionomer mixed with amalgam used as a base. However, these restorations do not bond as well to dentin as glass ionomer alone. Moreover, these materials have a tendency over time to discolor the dentin and provide an unsightly aesthetic appearance.

It is also desirable to develop a dental restoration system that works well with conventional materials, such as amalgam, to allow the tooth to be filled instead of using a crown or bridge, as amalgam is less expensive and is easy to handle.

OBJECTS OF THE INVENTION

Accordingly, it is one object of the present invention to provide a dental restoration method which is reliable, inexpensive and expedient.

It is another object of the present invention to provide a dental restoration system that does not require pins or acid etching.

It is another object of the present invention to provide a dental restoration system which bonds to dentin, fills dentin tubules and eliminates the need for unnecessary extraction.

It is another object of the invention to provide a dental restoration system that internally bonds the remaining crown of a tooth together so as to avoid continued cracking of the tooth enamel.

It is another object of the present invention to provide a dental restoration system which is able to strongly hold large amalgam fillings.

It is another object of the invention to provide an amalgam filling with an increased life expectancy.

It is another object of the invention that provide a restoration system that may be used with amalgam having a reduced mercury content.

It is another object of the invention to provide an amalgam filling strongly bonded to dentin.

SUMMARY OF THE INVENTION

Wet glass ionomer cement is applied to a tooth lesion. Before the cement hardens, wet amalgam is applied on top of the glass ionomer cement. The glass ionomer bonds to the tooth, and the interface of the wet cement and wet amalgam allows strong ionic bonds to form between the glass ionomer cement and the amalgam, to provide an exceptionally strong bond between the amalgam and the tooth.

DETAILED DESCRIPTION

A tooth lesion is first prepared to receive an amalgam filling using conventional techniques. If sufficient tooth structure is present, the tooth may be undercut to provide improved mechanical retention for the completed filling. Liquid glass ionomer is then applied to the prepared tooth lesion. The glass ionomer cement preferably has a set time of 5-10 minutes and contains fluoride ions to assist in preventing tooth decay by releasing fluoride ions into the dentin over time. Glass ionomer cement is available from a variety of sources including the GlasIonomer Cement, Type I distributed by Shofu Dental Corporations of Menlo Park, Calif. While the glass ionomer cement layer is still wet, a layer of wet amalgam, such as Valiant Phd, is placed disposed on the glass ionomer layer using conventional amalgam application techniques. The glass ionomer and amalgam layers are allowed to harden to form a solid laminate structure that sufficiently restores the preferred form of the tooth.

As noted above, the adhesion of glass ionomer cement to dentin is well documented. However, the present invention results in a remarkably strong bond between the glass ionomer cement and the amalgam, after the amalgam has hardened. The precise explanation for the bond is not fully appreciated, but it is believed that an ionic bond is created between the wet glass ionomer cement and the wet amalgam. Specifically, it is believed that because both constituents are interfaced while in a liquid state, the glass ionomer ions (having strong negative charges) and the metal particles (including tin) in the amalgam (having strong positive charges) are able to physically move and align themselves before the constituents harden. When aligned, a strong ionic bond is created between the constituents. This level of ionic bonding does not occur when wet amalgam is applied to a hardened glass ionomer layer as in the prior art. The nature of the ionic bond also suggests that bond strength may be increased by employing amalgam with an increased tin content, as the tin particles provide a particularly strong ionic bond. Likewise, increasing the fluoride content of the glass ionomer cement may increase the bond strength.

In another embodiment of the invention, amalgam powder is mixed with the glass ionomer cement before the cement is applied to the tooth. Preferably, the amalgam powder has substantially the same metals in the same percentage as the amalgam to be used as filling material, as this will reduce the risk of galvanic activity. The amount of amalgam powder may vary from about 2% to 50% by volume of the glass ionomer cement. Adding the amalgam powder to the glass ionomer cement provides several benefits. First, when first introduced, the amalgam powder initiates ionic activity in the glass ionomer by causing disassociation of the ions, thus preparing them to bond to the wet amalgam. Therefore, ionic bonds to the wet amalgam will occur at a higher rate. Because there is an overabundance of ions in the glass ionomer cement, there is no diminution in ions available to bond to the wet amalgam. Second, the subsequent bond to the amalgam will have an increased shear strength due to internal bonding in the cement with the amalgam particles.

Preliminary tests have shown the amalgam-glass ionomer bond strength to be about 40 psi, which is much stronger than conventional amalgam fillings without mechanical retention and the bond between glass ionomers and porcelain, or acrylic restorations. Thus, this method may be used to repair a tooth which might otherwise require extraction or a crown. Moreover, because the entire amalgam surface containing the glass ionomer cement is ionically bonded, the amalgam holds the tooth crown together to thereby prevent cracking. Also, the risk of exposing dental pulp to acid as used in other techniques is eliminated.

The present invention also allows use of an amalgam having a reduced mercury content. Specifically, the viscous glass ionomer cement layer fills small crevices which ordinarily are required to be filled by amalgam in a conventional filling. Since, in the present invention, amalgam does not fill the small crevices, the content of the amalgam need not be as fluid as is required for conventional fillings. The reduction of mercury content of fillings is very important in reducing the potential risk to the patient and to the dentist for undesirable exposure to mercury.

It will be appreciated by those of skill in the art that the restoration of major tooth lesions according to the present invention can be accomplished in instances where more expensive crowns or bridges would ordinarily be required. In addition, the procedure of the present invention can be accomplished in much less time. Moreover, due the strong ionic bond with the amalgam, the restoration will last longer than conventional amalgam fillings, even for large lesions. The use of glass ionomer cement seals dentin tubule, which helps eliminates post restorative sensitivity. Finally, since the glass ionomer cement may contain fluoride, it provides a fluoride release which assists in inhibiting recurrent decay.

I claim:

1. A method of restoring lesions in a living tooth, comprising the steps of:

applying a wet glass ionomer cement to the lesion;

placing a wet dental amalgam directly on the wet glass ionomer cement enabling the glass ionomer cement to bond the amalgam to the tooth; and allowing the wet glass ionomer cement and wet dental amalgam to harden, such that the glass ionomer cement is bonded to the amalgam.

2. The method of claim 1 wherein the wet dental amalgam includes tin.

3. The method of claim 1 wherein the glass ionomer cement further includes amalgam particles.

4. The method of claim 3 wherein the amalgam particles in the glass ionomer cement have substantially the same metallic composition as the metal particles of the wet dental amalgam.

5. The method of claim 1 wherein the bond between the layer of glass ionomer and the layer of amalgam has a bond strength greater than 10 psi.

6. The method of claim 5 wherein the bond between the layer of glass ionomer and the layer of amalgam has a bond strength of at least 40 psi.

7. A restoration for restoring lesions in a living tooth, comprising:

a layer of glass ionomer cement bonded to the tooth; and a layer of amalgam disposed on the layer of glass ionomer cement, the restoration having been formed according to the method of claim 1.

8. The restoration of claim 7 wherein the glass ionomer cement includes fluoride ions.

9. The restoration of claim 7 wherein the amalgam includes tin.

10. The restoration of claim 7 wherein the glass ionomer cement further includes amalgam particles.

11. The restoration of claim 10 wherein the amalgam particles in the glass ionomer cement have substantially the same metallic composition as the metal particles of layer of amalgam.

12. The restoration of claim 7 wherein the bond between the layer of glass ionomer and the layer of amalgam has a bond strength greater than 10 psi.

13. The restoration of claim 12 wherein the bond between the layer of glass ionomer and the layer of amalgam has a bond strength of at least 40 psi.

14. A tooth having a restored lesion, the restoration of the lesion being formed by the process of claim 1.

15. The tooth having a restored lesion of claim 14 wherein the bond between the glass ionomer cement and the amalgam is ionic.

16. The method of restoring lesions in a living tooth of claim 1 wherein the bond between the glass ionomer cement and the amalgam is ionic.

17. The restoration for restoring lesions in a living tooth of claim 7 wherein the bond between the glass ionomer cement and the amalgam is ionic.

* * * * *

REEXAMINATION CERTIFICATE (3948th)

United States Patent [19]
Arnold

[11] B1 5,252,122
[45] Certificate Issued Dec. 7, 1999

[54] IONIC BOND BETWEEN AMALGAM AND GLASS IONOMER

[75] Inventor: Thomas J. Arnold, Winslow, Ind.

[73] Assignee: Mion International Corporation, Winslow, Ind.

Reexamination Request:
No. 90/005,160, Nov. 17, 1998

Reexamination Certificate for:
Patent No.: 5,252,122
Issued: Oct. 12, 1993
Appl. No.: 07/942,375
Filed: Sep. 9, 1992

Related U.S. Application Data

[63] Continuation of application No. 07/748,679, Aug. 22, 1991, abandoned.

[51] Int. Cl.$^6$ ................. C09K 3/00; A61C 5/00
[52] U.S. Cl. ........................... 106/35; 433/228.1
[58] Field of Search ............. 106/35; 433/228.1

[56] References Cited

PUBLICATIONS

Hotz et al "The Bonding of Glass Ionomer Cements to Metal and Tooth Substrates", British Dental Journal p 43, 44, Jan. 18, 1977.

Scherer et al, "Reinforced Glass Ionomer Cement vs Zinc Phosphate Cement" NYS Dental Journal p 19, 20, Jan. 1990.

Baldwin, Cement and Amalgam Fillings, 18 J. Brit. Dental Ass'n 255 (1897).

Epsom, Modified Bonded Amalgam Technique (letter to the Editor), 156 Brit. Dental J. 38, Jan. 21, 1984.

Horton, Modified Bonded Amalgam Technique (letter to the Editor), 156 Brit. Dental J. 38, Jan. 21, 1984.

Youngston et al., "In Vitro" Marginal Microleakage: Examination of Measurements Used in Assessment, 18 J. Dentistry 142 (1990).

*Primary Examiner*—Margaret Einsmann

[57] ABSTRACT

Wet glass ionomer cement is applied to a tooth lesion. Before the cement hardens, wet amalgam is applied on top of the glass ionomer cement. The glass ionomer bonds to the tooth, and the interface of the wet cement and wet amalgam allows strong ionic bonds to form between the glass ionomer cement and the amalgam, to provide an exceptionally strong bond between the amalgam and the tooth.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–17 is confirmed.

* * * * *